United States Patent
Hessel et al.

[11] Patent Number: 5,531,738
[45] Date of Patent: Jul. 2, 1996

[54] PROCESS FOR OPERATING A LASER

[75] Inventors: Stefan Hessel, Munich; Frank Frank, Ebersberg; Gerhard Hauptmann; Werner Hiereth, both of Munich, all of Germany

[73] Assignee: Deutsche Aerospace AG, Munich, Germany

[21] Appl. No.: 352,569

[22] Filed: Dec. 9, 1994

[30]     Foreign Application Priority Data

Dec. 9, 1993 [DE] Germany ............... 43 41 967.4

[51] Int. Cl.⁶ ................................................. A61B 17/36
[52] U.S. Cl. ............................ 606/2; 606/11; 607/89
[58] Field of Search ........................... 606/2, 3, 11, 12, 606/14, 15; 607/88, 89, 92, 116; 128/898

[56]         References Cited

U.S. PATENT DOCUMENTS

| | | | |
|---|---|---|---|
| 4,887,600 | 12/1989 | Watson et al. | 606/15 |
| 5,312,392 | 5/1994 | Hofstetter et al. | 606/3 |
| 5,330,517 | 7/1994 | Mordon et al. | 606/2 |

FOREIGN PATENT DOCUMENTS

| | | |
|---|---|---|
| 3024169C2 | 1/1982 | Germany . |
| 3143421C2 | 5/1982 | Germany . |
| 3934647A1 | 4/1991 | Germany . |

OTHER PUBLICATIONS

Übersicht, Seite 630–634, "Thermische" Therapie der benignen Prostatahypperplasie. Author: R. Muschter, A. Hofstetter, 1992.

*Primary Examiner*—Stephen C. Pellegrino
*Assistant Examiner*—Sonya Harris Ogugua
*Attorney, Agent, or Firm*—Evenson, McKeown, Edwards & Lenahan

[57]         ABSTRACT

For an interstitial thermotherapeutic treatment of biological tissue in which, for generating a coagulation necrosis, the radiation of the laser within a radiation period is guided into the tissue by way of a fiber optic waveguide, the laser power is reduced continuously or in steps during the radiation period.

13 Claims, 1 Drawing Sheet

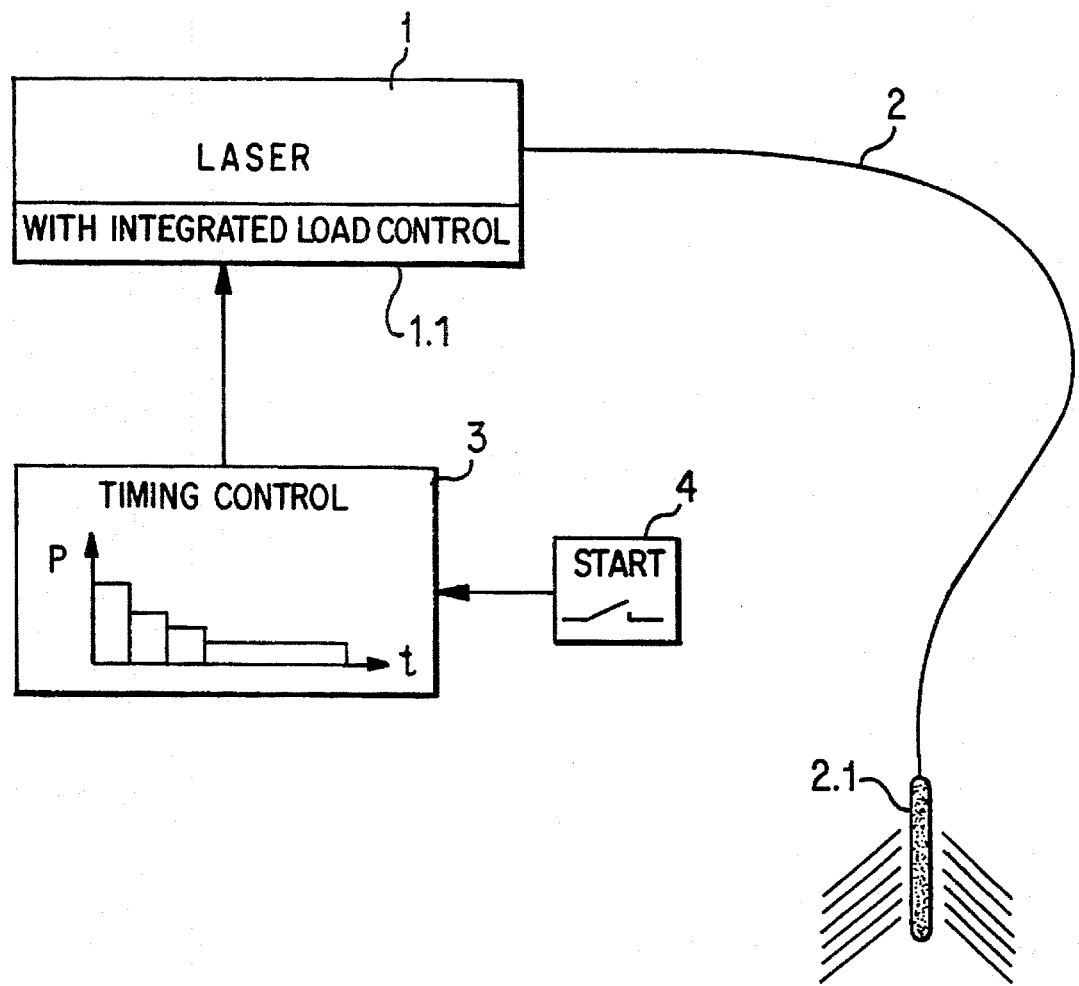

PROCESS FOR OPERATING A LASER

BACKGROUND AND SUMMARY OF THE INVENTION

This invention relates to a method for operating a laser for an interstitial thermotherapeutic treatment of biological tissue in which, for producing a coagulation necrosis, the radiation of the laser is guided into the tissue within a radiation period by way of a fiber optical waveguide.

In interstitial thermotherapy by means of laser radiation, a special-construction fiber optical waveguide (for example, according to European Patent Document EP 0 292 695 B1) is guided into the tissue to be heated. In this case, the application of the laser radiation causes a thermal denatuation of the tissue and therefore the formation of a coagulation necrosis. On the one hand, the effect of the applied laser radiation is determined by the laser parameters, such as the wave length, the duration of the radiation, the laser power and the power density and, on the other hand, by the tissue parameters, such as the absorption capacity, the scattering, the heat conduction, the tissue structure and the blood supply.

At temperatures of above 60° C., the tissue parameters will change, for example, as a result of coagulation, carbonization or closure of the blood vessels. Particularly, the tissue carbonization, for example, as the result of excessive laser power or excessive power density, leads to a drastic increase of the absorption capacity, whereby a deep penetration of the photons into the tissue is prevented. In addition, a carbonization of the tissue in the immediate surroundings of the fiber optic waveguide leads to an abruptly increased thermal stress of the fiber optic waveguide and may therefore cause its destruction. For this reason, up to now, the laser power has been adjusted to a value which is far below the destruction threshold for the fiber optic waveguide so that, on the one hand, it is ensured that neither the tissue will be carbonized during the radiation period, nor the fiber optic waveguide will be overloaded but that, on the other hand, a coagulation necrosis will be created which is sufficiently high.

However, for example, in the treatment of benign hyperplasia of the prostate, this has resulted in radiation periods of 10 minutes per puncture respectively in which case, on the average, 8 punctures are required for a treatment. In the case of the known method, this results in a total treatment duration of approximately 2 hours.

It is an object of the present invention to provide a method for operating a laser for an interstitial thermotherapeutic treatment of biological tissue which, while the above-mentioned boundary conditions are maintained, particularly for avoiding a tissue carbonization and a destruction of the fiber optic waveguide, permits a considerably shorter treatment duration.

This object is achieved by a method for operating a laser for an interstitial thermotherapeutic treatment of biological tissue in which, for generating a coagulation necrosis, the radiation of the laser is guided into the tissue by way of a fiber optic waveguide within a radiation period, characterized in that, during the radiation period, the laser power is reduced in a time-controlled manner continuously or in steps.

By means of a controlled continuous or step-by-step reduction of the laser power during a radiation period after the fiber optic waveguide punctures the tissue, the invention takes into account the complex occurrence of the heat conduction at the transition between the fiber optic waveguide and the tissue, which is present particularly in the case of the interstitial treatment by means of fiber optic waveguides. In the case of the initially cold tissue, a much higher laser power may be applied for a short time until the carbonization temperature has been reached. Since, by means of the heating of the tissue by way of the applied laser radiation, a heat transfer takes place at the same time by way of the surrounding tissue, which, however, is continuously reduced as the heating increases, the laser power is reduced continuously or step-by-step during the radiation period from the value, which initially is limited only by the maximum power of the laser or of the destruction threshold of the light-guiding components, such that the carbonization temperature of the tissue is not exceeded in the radiation period. Thus, the radiation duration for generating a coagulation necrosis of an equal size is reduced to approximately half the previous radiation time.

In contrast to measures involving control techniques, the power reduction of the laser, which takes place in a controlled manner, can be implemented without any problem by means of the known lasers provided for medical applications.

Furthermore, the method according to the invention has the effect that blood vessels situated in the surroundings of the used fiber optic waveguide are closed considerably faster and therefore a clear reduction of the heat removal is achieved by convection. The coagulation temperature at the transition between the fiber optic waveguide and the tissue is also achieved much more rapidly.

The optimal control curve for the reduction of the laser power is mainly a function of the tissue and is advantageously determined empirically. For most treatment cases, an initial laser power of maximally 25 watts with a continuous reduction during the radiation period to minimally 5 watts was found to be useful.

Other objects, advantages and novel features of the present invention will become apparent from the following detailed description of the invention when considered in conjunction with the accompanying drawings.

BRIEF DESCRIPTION OF THE DRAWINGS

The single drawing figure schemetically depicts a preferred embodiment of the present invention.

DETAILED DESCRIPTION OF THE DRAWINGS

A fiber optic waveguide 2, whose distal end is provided with a circumferentially radiating tip 2.1 for an interstitial thermotherapeutic treatment, is connected to an Nd:YAG laser in the power class of 40 watts with an integrated power control 1.1 which is suitable for medical applications. This tip 2.1 is pierced into the tissue to be treated, for generating a coagulation necrosis. The power control 1.1 of the laser is controlled by way of a time sequence control 3 which, in the illustrated embodiment, generates a step-by-step power reduction of the laser. The time sequence control 3 is switched on by means of a starting switch 4.

The time sequence control 3 determines the duration of a radiation period, the laser power P at the start and at the end as well as the control curve (stepped or continuous).

In the case of an in-vitro test on liver tissue, comparative interstitial treatments were carried out using conventional constant laser power and reduced laser power according to the invention during a radiation period. The results show that, by means of the radiation concept according to the invention, on the one hand, a clearly lower total energy is required for a given amount of coagulation than in the case of the use of a constant laser power and, furthermore, a reduction of the radiation duration was achieved to one half. While, in the case of a constant laser power, during a radiation period of 10 minutes, the power has to remain limited to 7 watts, in which case a coagulation necrosis in the form of an ellipsoid with the axes 18×24 mm was generated by means of a total applied energy of 4,200 J, in the case of the radiation concept according to the invention, the laser power is reduced from initially 20 watts in a step-by-step manner to 7 watts, in which case, during a radiation period of 5 minutes, a total energy of 2,820 J is applied and a coagulation necrosis is obtained which measures 21×29 mm.

In the case of these in-vitro tests, the laser power was reduced only in relatively rough steps so that a further improvement of the treatment result should be expected by means of a continuous optimized control curve.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. Method for operating a continuous wave laser generating radiation under laser power for an interstitial thermotherapeutic treatment of biological tissue generating a coagulation necrosis in a volume range of at least several cm$^3$, the method comprising the steps of:

guiding the radiation of the laser into the tissue interstitially by way of a fiber optic waveguide within a radiation period; and reducing the laser power under a time sequence control during the radiation period.

2. Method according to claim 1, wherein the laser power is reduced during the radiation period in such a manner that a temperature within the coagulation necrosis remains slightly below a carbonization temperature of the tissue receiving the radiation.

3. Method according to claim 1, further comprising the step of selecting an initial laser power within the radiation period in accordance with a destruction threshold value for the fiber optic waveguide.

4. Method according to claim 1, wherein the laser power is reduced during the radiation period from maximally 25 watts at a start of the radiation period to minimally 5 watts at an end of the radiation period.

5. Method according to claim 1, wherein the laser power is reduced continuously during the radiation period.

6. Method according to claim 1, wherein the laser power is reduced stepwise during the radiation period.

7. Method according to claim 2, wherein an initial laser power within the radiation period is determined by a destruction threshold value for the fiber optic waveguide.

8. Method according to claim 2, wherein the reduction of the laser power occurs within a radiation period at a rate of $1/t^3$ (t=time).

9. Method according to claim 3, wherein the reduction of the laser power occurs within a radiation period at a rate of $1/t^3$ (t=time).

10. Method according to claim 1, wherein the laser power is reduced during the radiation period from maximally 25 watts at a start of a radiation period to minimally 5 watts at an end of radiation period.

11. Method according to claim 7, wherein the laser power is reduced during the radiation period from maximally 25 watts at a start of the radiation period to minimally 5 watts at an end of the radiation period.

12. Method according to claims 9, wherein the laser power is reduced during the radiation period from maximally 25 watts at a start of the radiation period to minimally 5 watts at an end of the radiation period.

13. Method for operating a continuous wave laser generating radiation under laser power for an interstitial thermotherapeutic treatment of biological tissue generating a coagulation necrosis, the method comprising the steps of:

guiding the radiation of the laser into the tissue by way of a fiber optic waveguide within a radiation period; and reducing the laser power in a time-controlled manner during the radiation period at a rate of $1/t^3$ (t=time).

* * * * *